United States Patent
Sjöqvist

(10) Patent No.: US 6,409,660 B1
(45) Date of Patent: Jun. 25, 2002

(54) PORTABLE TELEMEDICINE DEVICE

(75) Inventor: Bengt Arne Sjöqvist, Tärneskärsgatan (SE)

(73) Assignee: Ortivus AB, Vastra Frolunda (SE)

( * ) Notice: Subject to any disclaimer, the term of this patent is extended or adjusted under 35 U.S.C. 154(b) by 0 days.

(21) Appl. No.: 09/254,428
(22) PCT Filed: Sep. 19, 1997
(86) PCT No.: PCT/SE97/01587
§ 371 (c)(1), (2), (4) Date: May 10, 1999
(87) PCT Pub. No.: WO98/11820
PCT Pub. Date: Mar. 26, 1998

(30) Foreign Application Priority Data

Sep. 19, 1996 (SE) ................................................ 9603428
Sep. 19, 1996 (SE) ................................................ 9603429

(51) Int. Cl.⁷ ................................................ A61B 5/00
(52) U.S. Cl. ........................ 600/300; 600/512; 128/904
(58) Field of Search ............................... 600/300–301, 600/481–486, 500–509, 544–545, 529, 538; 128/900, 903–904; 705/2, 3

(56) References Cited

U.S. PATENT DOCUMENTS

| | | | |
|---|---|---|---|
| 4,827,943 A | * 5/1989 | Bornn et al. | 600/300 |
| 5,375,604 A | 12/1994 | Kelly et al. | |
| 5,549,113 A | * 8/1996 | Halleck et al. | 128/903 |
| 5,579,775 A | * 12/1996 | Dempsey et al. | 128/903 |
| 5,687,717 A | * 11/1997 | Halpern et al. | 600/300 |
| 5,752,917 A | * 5/1998 | Fuchs | 600/484 |
| 5,967,975 A | * 10/1999 | Ridgeway | 600/300 |
| 6,038,469 A | * 3/2000 | Karlsson et al. | 600/509 |

FOREIGN PATENT DOCUMENTS

| | | |
|---|---|---|
| EP | 0 251520 | 1/1988 |
| EP | 0 635781 | 1/1995 |
| EP | 0 669715 | 8/1995 |
| EP | 0 707825 | 4/1996 |
| SE | A9001549-6 | 10/1991 |

* cited by examiner

Primary Examiner—Robert L. Nasser
Assistant Examiner—Michael Astorino
(74) Attorney, Agent, or Firm—Birch, Stewart, Kolasch & Birch, LLP

(57) ABSTRACT

A portable telemedicine device used in prehospital, preliminary diagnostic procedures and treatments includes a data processing unit for receiving and processing data. Measurement devices for determining patient data relative to a predetermined patient. Presentation device for displaying patient data received from the measurement devices. Entry device for manually inputting manual data into the data processing unit. Communication equipment for permitting bidirectional communication with at least one central unit for transmitting manually entered manual data and patient data to the central unit and to receive information data from the central unit representing results from diagnoses, suggested care and previously stored data on the predetermined patient. A predetermined number of the data processing unit, measurement devices, presentation device, entry device and communication equipment being integrated into a portable unit. A device for assigning priorities to the information data, the patient record file data, physiological data, form data, numbers, images upon transmission of the data to the central unit for ensuring that a highest priority data in a predetermined situation is transmitted first.

16 Claims, 4 Drawing Sheets

|  | 214365-8790 | Putte Patient |  | CASE RECORD FILE |
|---|---|---|---|---|

Personal Code No.   214365-8790
Name: Putte Patient

| BP syst_____ | Resp. rate. 110 | Suturation  98 |
|---|---|---|
| BP diast_____ | Pulse        127 | Smart VAS |

Eye movement    3 open when addressed firmly
Motor response
Verbal response
GCS

Diagnosis
  suspected infraction
  angina pectoris
  heart failure
  diffuse chest pains Skin
  ☐ Normal
  ☐ Damp
  ☐ Pale
  ☐ Cyanosis Priority before action Change form Main Menu
Text Stop Main Menu

Fig. 4

PORTABLE TELEMEDICINE DEVICE

TECHNICAL FIELD

The present invention concerns a portable tele medicine device for use in preliminary diagnostic procedures and treatments.

BACKGROUND

The normal procedure in the case of serious illnesses is to transport the patient to a hospital for diagnosis and treatment of the illness. However, it has proved to be advantageous to arrange for the nursing or ambulance staff to carry out the diagnosis and to start the treatment already at the place of patient pick-up. Such an arrangement likewise makes it possible to establish at an early stage whether a particular specialist competence and special equipment or the like are required, whereafter the patient may be transported straight to the place where such competence, equipment etcetera are available.

Such early diagnosis and treatment would be considerably facilitated, were the nursing staff given a possibility to carry with them a portable telemedicine device adapted to register signals from ECG and VCG units and similar sensing equipment. A portable unit of this kind, which may be docked and thus be connected to a stationary communications network (LAN), which allows connection thereto of external measurement equipment, and which comprises a display device for visualisation of the measurement results, is disclosed in U.S. Pat. No. 5,375,604.

However, this prior-art device is merely a passive unit and it is designed for reception and visualisation only of signals from the measurement equipment. It cannot be used to establish active contact with and an exchange of information between the patient-attending staff and other individuals, a possibility which could be helpful in the diagnosis procedure as well as for the implementation of correct treatment measures. This is true particularly in the case of the above portable unit when used un-docked, in which case there is no communication with other equipment.

Furthermore, U.S. Pat. No. 5,441,047 describes a system according to which selected data on the patient is collected automatically, whereupon said data are forwarded via a stationary telecommunication network, such as a cable television network, to a center where the diagnosis, monitoring or similar operations may be performed. The referred-to equipment is not, however, portable and in addition it comprises a plurality of independent components, and consequently this equipment is not adapted for ambulatory use and positioning onboard e.g. an ambulance. Nor is it adapted for active exchange of information between the nursing staff by the patient's side and the personnel at the central unit.

In addition, there is a need for message exchanges between the nursing staff by the patient's side and the personnel at the central unit as well as for possibilities of filling in certain types of pre-defined forms, such as patient case record files, already in the initial stage by the patient's side. These needs are not met in the prior-art devices.

In addition, it would be desirable, were it possible to enter data manually and preferably by one hand only, in a convenient, rapid and simple manner. It would likewise be desirable, were it possible to construct the entry means sufficiently small not to make the portable equipment unnecessarily voluminous and unmanageable.

PURPOSE OF THE INVENTION

The object of the present invention thus is to provide a portable telemedicine device which completely or at least partly eliminates the problems encountered in connection with the prior-art technology.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and of the scope of the invention will become apparent to those skilled in the art form this detailed description.

BRIEF DESCRIPTION OF THE DRAWING FIGURES

The present invention will become more fully understood from the detailed description given hereinbelow and the accompanying drawings which are given by way of illustration only, and thus are not limitative of the present invention, and wherein:

FIG. 4 illustrates a second example of a display layout intended for use together with the device of FIG. 2.

DETAILED DESCRIPTION OF PREFERRED EMBODIMENTS

The invention will be described in closer detail in the following for exemplifying purposes with reference to the accompanying drawings.

Figure 1:
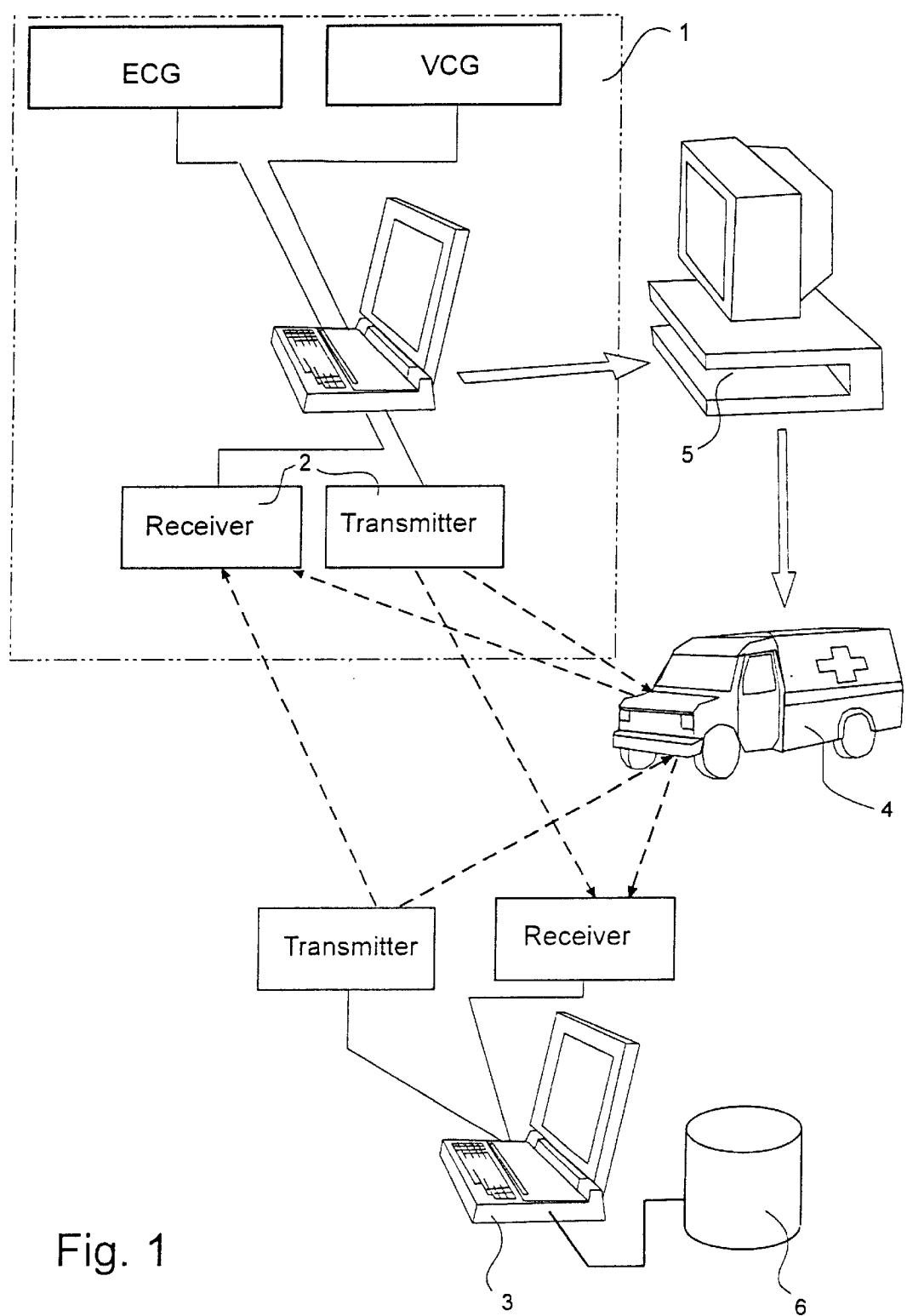
FIG. 1 is a schematic view of a system comprising a portable telemedicine device in accordance with the invention.

As shown in FIG. 1, the invention comprises a portable telemedicine device 1 including integrated measuring equipment, such as ECG and VCG, input means for connecting external measuring sensors, a display for displaying the measurement data and the like, entry means for entry of other measurement data, patient's name, observations and so on, and communication equipment 2. The portable telemedicine device in accordance with the invention preferably is an easily manageable, integrated unit, illustrated in FIG. 2. Preferably, this unit is also provided with a rechargeable battery unit, which adds to the ambulatory nature of the device.

Again referring to FIG. 1, the communication equipment 2 may be arranged to transmit digital data via a mobile telephone network, such as GSM or the like, via the MOBITEX network or by any other suitable means. Thus, the telemedicine device may communicate directly with one or several central units 3 or via one or several intermediate stations, such as for instance an ambulance 4. Optionally, the communication may be established via option communication means, such as GSM and MOBITEX, as selected in accordance with the conditions- in each individual case.

Preferably, the central units are data-processing devices capable of receiving information data and presenting the latter in real time, and also capable of emitting information data to portable units. The central unit preferably also is capable of communicating with other systems, if storing information data, and of later displaying such stored information data. However, central units of this nature are previously known within the technical field concerned and the design of these units does not form part of the present invention, although they do form part of a system comprising the portable telemedicine device in accordance with the invention.

The portable telemedicine device is further advantageously equipped with a connecting interface for allowing convenient docking thereof to stationary equipment 5, e.g. onboard an ambulance or inside a hospital. The docking interface may be designed to shift its mode of communication at the instance of docking, to allow transmission via another telecommunication network or via cables coupled to the stationary equipment. In addition, the docking may involve connection to network voltage, battery chargers, external entry means (such as keyboards), external displays, and so on. Optionally, the portable telemedicine device could likewise be adapted for communication via IR transmission using prior-art equipment, such as PDA equipment (Personal Digital Assistant) and the like.

The device may also be adapted for automatic selection of a telecommunication network in response to the current reception conditions, in order thus to offer the best possible transmission performance, Such adaptation could likewise depend on the type of information data to be transmitted and on the manner of the transmission. In this way it becomes possible to use different networks for transission for example of large data volumes that must be transmitted to a receiver within a brief space of time, and of short messages that are to be transmitted to several receivers. For instance, the device-may utilise-networks of such a different nature as the circuit-switched GSM network and the packet-switched MOBITEX. However, to achieve this versatility feature, adaptations are required in the form of different software as well as different hardware. To make it possible to use such a comparatively slow transmission system as the MOBITEX, selection and pre-processing of data are required as is also compressing of these data.

When the portable telemedicine equipment is intended for use by ambulance staff or other ambulant personnel, it is advantageously brought along when the ambulance staff is called to the patient. The sensors associated with ECG, VCG etcetera are connected, and a first diagnosis may then be made. In some cases it may, however, be more appropriate to defer connection of the equipment until the patient is onboard the ambulance.

The display preferably is divided into different fields, showing for example:

Information on the patient's name, patient ID number, time, and so on;

Monitoring information received from the measuring equipment, such as continuous ECG monitoring, blood pressure monitoring, continuous curves indicating the variations in the oxygenation of the blood, and so on;

ECG reports, "cuttings" from real-time curve graphs, tendencies, patient case record files, other information, recently received messages, and so on;

Up-to-date values of collected measurement data and set alarm limits;

Menu of currently selectable commands;

Status of communication equipment, such as available connected receivers and the band width of the communication channel;

Messages received and emitted, inclusive of facilities for browsing through old messages;

Setting options, e.g. different communication networks, reception and transmission via ambulance or not, different areas of application, choice of external equipment to be connected, and so on.

In addition, the menu system could advantageously be designed to comprise several levels, including one main menu and one or several levels including sub-menus.

Following connection of the equipment, information data are entered, either automatically via the measuring instruments or manually by the patient-attending staff. Some information data, such as those relating to certain measurement results, annotations entered into patient case record files, patient information and so on, are then transmitted automatically to-the predetermined receivers to which the device is connected, whereas other information data are forwarded only as ordered by the attending staff. A transmission list determines which receivers are to be used in each individual case, from which list one or several central units may be preselected. Preferably, the list may be altered in the process of use.

The information to be transmitted may be assigned different priorities, the information data most essential for correct diagnosis and for the implementation of correct treatment being given a higher priority and being transmitted prior to information data of less importance. This feature is particularly advantageous for instance when the capacity of the communication network is such that the latter is slow in transmitting the information and when it may not even be possible to transmit all information. The priority feature may be implemented manually, or, which in most cases is the preferred alternative, automatically with the aid of software, or else a combination of the two varieties is possible. The medical usefulness should, at all times, govern the priority.

In addition, the portable telemedicine equipment is supplied with information data from the central unit, on the one hand in the form of messages from e.g. specialist physicians, the coordinating control group, etcetera, and on the other in the form of data from the patient's case record file and the like, data which are already stored in databases 6 in the central unit.

In addition to its use in showing measurement results, the portable telemedicine device in accordance with the invention could also be used for filling in certain forms, such as patient's case record files and the like, in addition to which it offers facilities for communication with a central unit (or several central units) via the telecommunication network. The central unit could be positioned e.g. in the closest large hospital where the received information data could be examined by specialist physicians of the relevant medical discipline and a correct decision be taken rapidly, both with respect to the treatment to be implemented right away and to the planning and the preparations for the continued treatment. In other words, owing to the communication facility, measurement results and other entered information data are transmitted in full or in part from the portable telemedicine equipment to the central unit, and the information data, which may include treatment counselling, queries relating to the diagnosis, information regarding where to transport the , and so on, are transmitted from the central unit to the portable unit. In addition, all dialogue preferably should be stored in the portable unit and/or the central unit.

The various part components of the device are, as already mentioned, preferably integrated in an easily manageable unit, thus making it simple to handle, and versatile and easy to transport and to connect.

Optionally, additional equipment could be included as parts of the device or be connectable thereto, such as printers, cameras, microphones, loud-speakers, etcetera, depending on need, communication channel capacity and so on.

According to a particularly preferred embodiment the portable unit is provided with an entry means of a special design and forming part of the present invention.

Figure 2:
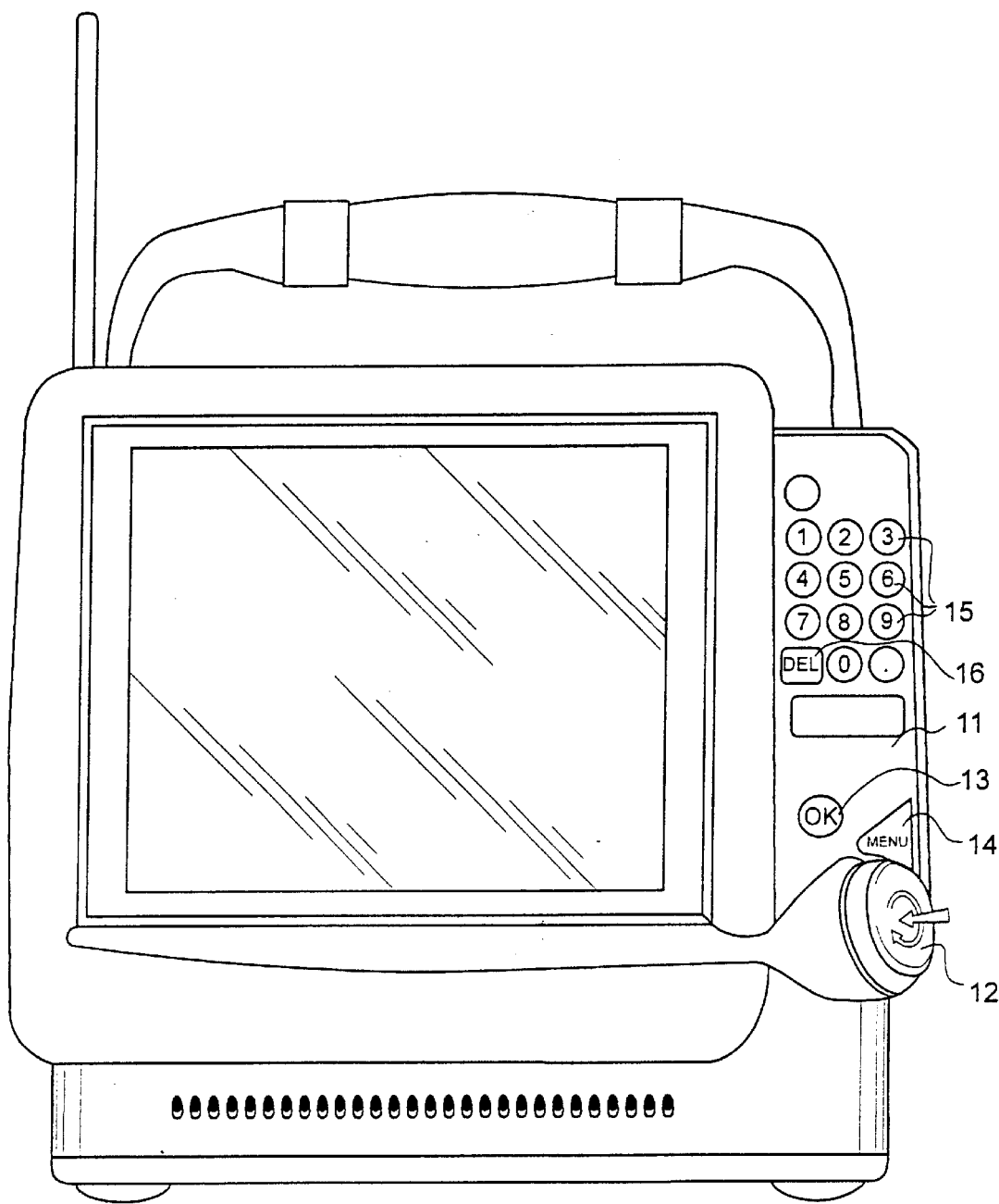
FIG. 2 is a view of a preferred embodiment of the portable telemedicine device of FIG. 1.

As appears from FIG. 2, the entry means comprises a r bottom plate 11 formed with an entry means consisting of a rotatable and depreciable actuating member 12 in the form of e.g. a ball or a wheel, and of additional entry buttons 13 and 14. The actuating member affects a cursor on the display screen in such a manner that the cursor moves in response to actuation of the actuating member. The cursor is only movable backwards and forwards between points in a predetermined order. For instance, the cursor movement could be upwards and downwards in a vertically arranged menu, jumping between a number of different windows on the screen or the like. Upon depression of the actuating member 12 the object highlighted at that moment by the cursor is activated (i.e. the function identical to that of the "ENTER"-key on an ordinary keyboard). In this situation, either the indicated function is performed, involving for instance entering an object in the form, or else a sub-menu appears, whereupon the procedure is repeated.

In this manner it likewise becomes possible to enter text or figures, in that by turning the actuating member the operator may proceed through the entire alphabet or the numbers and by depressing the member indicate the letters or figures he wants to enter.

Out of the extra entry buttons of the entry means, one button 13 is for verifying incoming messages or alarms and one button 14 for moving to a superior menu level. In addition to these two buttons the entry means could be supplemented with numeric keys 15 representing digits 0–9 etcetera, in order to render the data input more efficient, should the entry items comprise several measurement values in digit form. In addition, the entry means preferably comprises a delete button 16 to erase entered values.

An entry means in accordance with the invention occupies but a fraction of the space required by a conventional keyboard, in addition to which it could advantageously be placed vertically, a position most unsuitable for conventional keyboards. For instance, an LCD display and an associated, e.g. juxtaposed entry means in accordance with the invention may easily be placed in positions where conventional terminals cannot be used. In addition, the entry of input data may easily be effected using one hand only.

Figure 3:
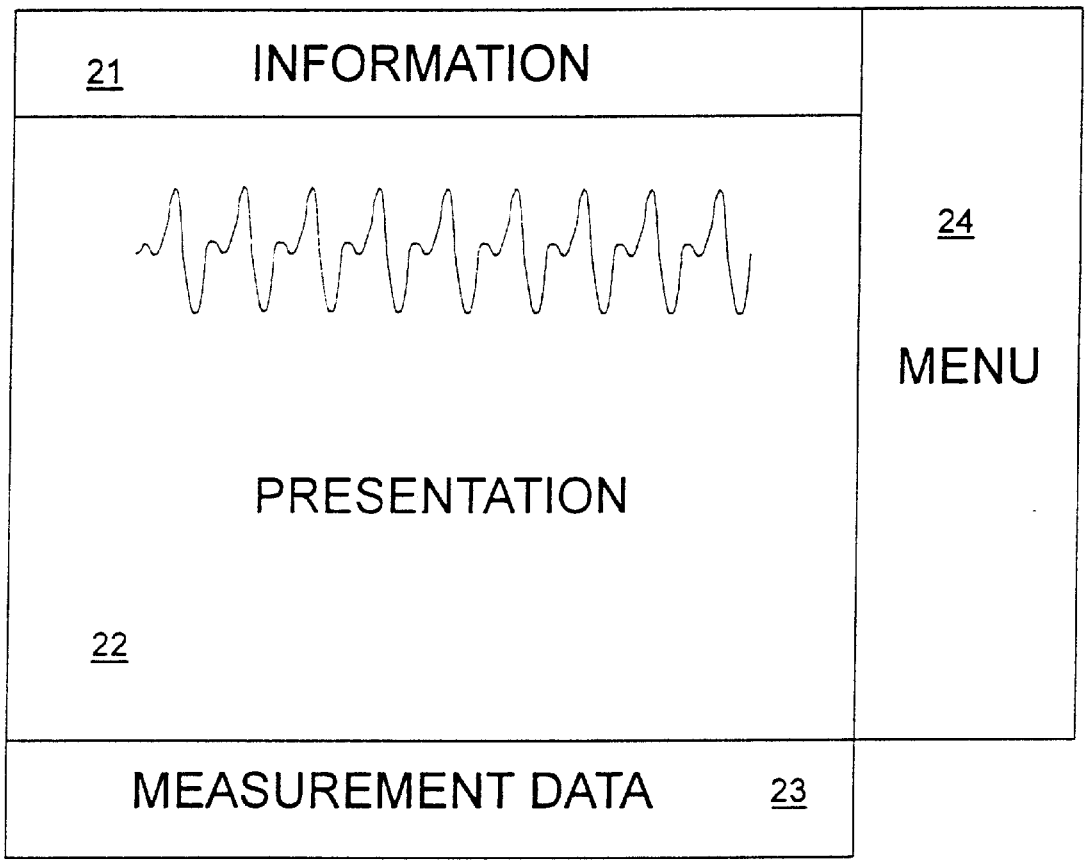
FIG. 3 illustrates a first example of a display layout intended for use together with the device of FIG. 2.

When the entry means is used as described above, the display preferably is divided into several fields, such as shown for example in FIG. 3. In this drawing figure is illustrated one example of a display layout that may be used by the medical services and that comprises one field 21 containing information on the patient's name, identity number, information on the status of the communication and similar comprehensive information, a second field 22 containing a presentation, for instance in the form of curve graphs, representing incoming measurement values and the like (e.g. from ECG), a third field 23 containing measurement data derived from other (or the same) measurement instruments and alarm limits, and a fourth field 24 containing a menu of selectable options. As the actuating member is being rotated different menu options will be highlighted in a predetermined order. This predetermined order could be e.g. from the top towards the bottom, or inversely, depending on the direction in which the operator rotates the actuating member. The highlighted option is activated upon depression of the actuating member, causing either the activation of a function or the appearance of a new sub-menu.

FIG. 4 illustrates one example of the configuration of a display upon activation of a "case record file" function for entering information data into the patient's case record file. Under this option heading, a sub-menu appears. In this case, the sub-menu comprises four different case record fields and three additional menu options. To enter data, the operator/attendant turns e.g. the actuating member 12, causing the first case record field to be highlighted, whereupon he depresses the actuating member to activate the highlighted field. In this field, there are two alternative choices: input of personal code number and input of personal name. As the personal code number is entered, this option is highlighted in the same manner as mentioned above, whereupon one digit at a time is entered. This could be achieved e.g. by means of a line of numbers which appears on the display and from which desired numbers are chosen through rotation and depression of the actuating member as indicated previously. Alternatively, the highlighted number is increased or decreased by means of rotation of the actuating member, followed by depression of the member, the corresponding number thus being chosen and the cursor made to proceed to the next position, wherein the procedure is repeated.

In order to return to the immediately superior menu the latter could either be permanently available as a last selectable menu option or else be retrieved by use of the particular return button. An entered digit could be cancelled/deleted with the aid of the button provided for this purpose.

Entry of letters is effected in the same manner as entry of figures, and figures as well as letters and also other signs may be selectable in all positions.

In addition, the entry procedure could in many cases be simplified, when only a restricted amount of entry options exists or occurs frequently. In such cases, the data entry could be effected via a menu comprising predefined options, such as shown for example in the fourth, lowest case record field in FIG. 4. In this field, the diagnosis, such as "angina pectoris"; may be entered by advancing the cursor through rotation of the actuating member until the cursor reaches the relevant option, and by subsequently marking the latter as indicated above.

Several modifications of the entry means in accordance with the invention are conceivable. For instance, the entry means need not comprise supplementary entry buttons but the rotatable and depressible actuating member by itself suffices in many cases. In addition, the actuating member could optionally be divided into two separate means, one of which is rotatable whereas the other is depressible. Several modifications of other parts of the invention are of course likewise possible. For example, other measurement equipment than that mentioned in the aforegoing may be coupled to the device. The device could furthermore be used in other applications involving services and activities related to nursing and attending of individuals, such as home-help services. Such closely related varieties of the invention must be regarded to be within the scope of the invention as the latter is defined in the appended claims.

What is claimed is:

1. A portable telemedicine device used in prehospital, preliminary diagnostic procedures and treatments comprising:
   at least one measurement device for obtaining patient related information;
   an entry device for manual input of information;
   communication equipment for permitting bidirectional communication with at least one central unit for transmitting data to the central unit and to receive information data from the central unit; and
   means for assigning priorities to different types of information upon transmission of data to the central unit, said priorities being based on the medical usefulness of the information type, and for ensuring that the information type of highest priority in a predetermined situation is transmitted first.

2. The telemedicine device according to claim 1, wherein the device is used outside medical-care centers.

3. The telemedicine device according to claim 1, wherein the device is used outside hospitals.

4. The telemedicine device according to claim 1, wherein the device is used outside clinics.

5. The telemedicine device according to claim 1, wherein the device is used outside nursing homes.

6. The telemedicine device according to claim 1, wherein the communication is established via a wireless telecommunication network.

7. The telemedicine device according to claim 6, wherein the communication is established via GSM.

8. The telemedicine device according to claim 6, wherein the communication is established via MOBITEX.

9. The telemedicine device according to claim 1, further comprising means for docking the device with a base unit.

10. The telemedicine device according to claim 9, wherein the base unit is positioned onboard an ambulance.

11. The telemedicine device according to claim 9, and further including communication equipment operatively connected to said base unit for bidirectional communication with said central unit.

12. The telemedicine device according to claim 1, wherein said bidirectional communication is established with a plurality of central units.

13. The telemedicine device according to claim 11, further including means for automatically selecting, for said bidirectional communication, a communication link among a plurality of communication links based on which is most efficient for the current application.

14. The telemedicine device according to claim 1, wherein said entry means includes a rotatable actuating member for controlling a cursor on the presentation means for highlighting alternative objects in a predetermined order by rotation of the actuation member and a depressible actuation member for activating the current highlighted objects by depression of said depressible actuation member.

15. The telemedicine device according to claim 14, wherein the rotatable and depressible actuating member is combined into one single actuating member.

16. The telemedicine device according to claim 15, wherein the option objects to be highlighted form a main menu wherein each object may comprise several levels of sub-menus and said entry means also includes a return button for return to the level above the current level.

\* \* \* \* \*